US011807668B2

United States Patent
Li et al.

(10) Patent No.: US 11,807,668 B2
(45) Date of Patent: Nov. 7, 2023

(54) **USE OF CITRONELLOL IN PREPARING PREPARATION FOR PROMOTING EXPRESSION OF VIRULENCE GENE *TOXA* OF *PSEUDOMONAS AERUGINOSA***

(71) Applicant: Institute of Microbiology, Guangdong Academy of Sciences (Guangdong Detection Center of Microbiology), Guangzhou (CN)

(72) Inventors: Wenru Li, Guangzhou (CN); Xiaobao Xie, Guangzhou (CN); Taohua Zeng, Guangzhou (CN); Zhiqing Zhang, Guangzhou (CN); Jingxia Liu, Guangzhou (CN); Qingshan Shi, Guangzhou (CN)

(73) Assignee: INSTITUTE OF MICROBIOLOGY, GUANGDONG ACADEMY OF SCIENCES (GUANGDONG DETECTION CENTER OF MICRORI, Guangzhou (CN)

( * ) Notice: Subject to any disclaimer, the term of this patent is extended or adjusted under 35 U.S.C. 154(b) by 0 days.

(21) Appl. No.: 17/778,018

(22) PCT Filed: Oct. 27, 2021

(86) PCT No.: PCT/CN2021/126812
§ 371 (c)(1),
(2) Date: May 19, 2022

(87) PCT Pub. No.: WO2022/068954
PCT Pub. Date: Apr. 7, 2022

(65) Prior Publication Data
US 2023/0010612 A1   Jan. 12, 2023

(30) Foreign Application Priority Data
Apr. 22, 2021 (CN) .......................... 202110435173.6

(51) Int. Cl.
*C07K 14/21* (2006.01)
*C12N 1/20* (2006.01)

(52) U.S. Cl.
CPC ................ *C07K 14/21* (2013.01); *C12N 1/20* (2013.01)

(58) Field of Classification Search
CPC .... C07K 14/21; C12N 1/20; C12R 2001/385; C12P 21/02; Y02A 50/30
See application file for complete search history.

(56) References Cited

FOREIGN PATENT DOCUMENTS

CN   113201473 A   8/2021
WO   0218342 A2   3/2002

OTHER PUBLICATIONS

Aguilar et al., "The atu and liu clusters are involved in the catabolic pathways for acyclic monoterpenes and leucine in Pseudomonas aeruginosa", Applied and Environmental Microbiology, vol. 72, No. 3, pp. 2070-2079, 2006 (Year: 2006).*
Boukhris et al., "Chemical composition and biological activities of polar extracts and essential oil of rose-scented geranium, *Pelargonium graveolens*", Phytotherapy Research, vol. 27, p. 1206-1213, 2013 (Year: 2013).*
Ganesh et al., Chapter 3 Alternative Strategies to Regulate Quorum Sensing and Biofilm Formation of Pathogenic Pseudomonas by Quorum. Biotechnol. Appl. Quorum Sensing Inhibitors., 2018, Chapter 3, pp. 33-61. (Year: 2018).*
Gonzalez et al., Transcriptome Analysis of Pseudomonas aeruginosa Cultured in Human Burn Wound Exudates. Front. Cell. Infn. Microbiol., 2018, vol. 8, Article 39, pp. 1-14 (Year: 2018).*
Li et al., Diallyl disulfide from garlic oil inhibits Pseudomonas aeruginosa virulence factors by inactivating key quorum sensing genes. Appl. Microbiol. Biotechnol., 2018, vol. 102: 7555-7564. (Year: 2018).*
Wikipedia-Citronellol, 4 (four) pages, Retrieved from https://en.wikipedia.org on Mar. 23, 2023. (Year: 2023).*
Fakhri Haghi, et al., Effect of subinhibitory concentrations of imipenem and piperacillin on Pseudomonas aeruginosa toxA and exoS transcriptional expression, New Microbes and New Infections, 2019, pp. 1-14.
Xiaomei Hu, Research progress of exotoxin A gene expression in Pseudomonas aeruginosa, Progress in Microbiology and Immunology, 2004, pp. 73-75, vol. 32 No. 3.
Marko Davinic, et al., Role of Vfr in regulating exotoxin A production by Pseudomonas aeruginosa, Microbiology, 2009, pp. 2265-2273, vol. 155.

* cited by examiner

*Primary Examiner* — Ganapathirama Raghu
(74) *Attorney, Agent, or Firm* — Bayramoglu Law Offices LLC

(57) ABSTRACT

A use of citronellol in preparing a preparation for promoting an expression of a virulence gene toxA of *Pseudomonas aeruginosa* is disclosed. It was found that citronellol slightly inhibits the growth of a *Pseudomonas aeruginosa* PAO1 strain and can promote the transcription of the toxA of *Pseudomonas aeruginosa*, which can increase the yield of an exotoxin A, namely, an encoded product of toxA. Therefore, citronellol is applicable to the preparation of a preparation for promoting the expression of the virulence gene toxA of *Pseudomonas aeruginosa*.

Figure 1:
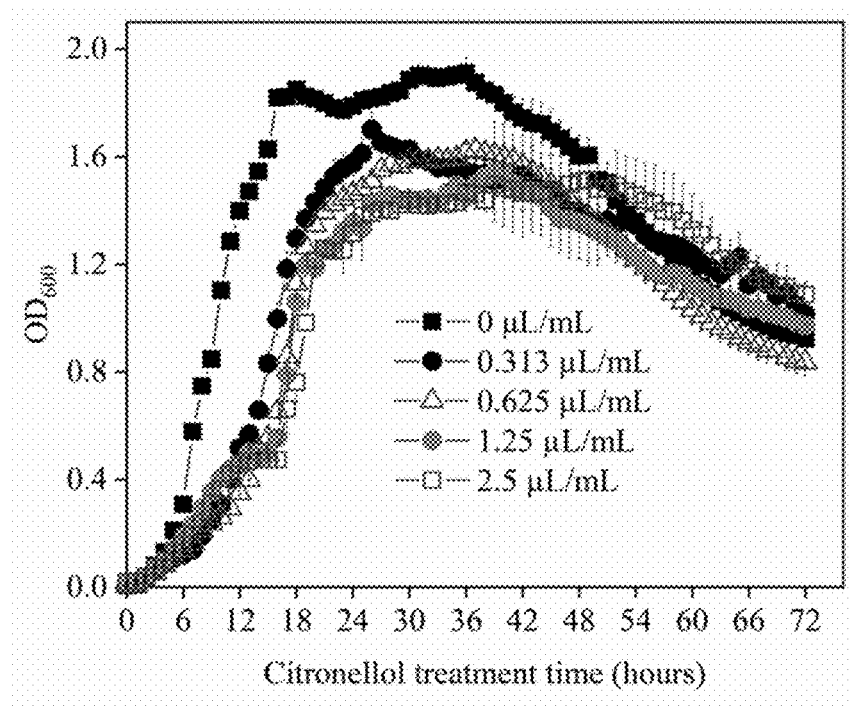

5 Claims, 1 Drawing Sheet
Specification includes a Sequence Listing.

USE OF CITRONELLOL IN PREPARING PREPARATION FOR PROMOTING EXPRESSION OF VIRULENCE GENE *TOXA* OF *PSEUDOMONAS AERUGINOSA*

CROSS REFERENCE TO THE RELATED APPLICATIONS

This application is the national phase entry of International Application No. PCT/CN2021/126812, filed on Oct. 27, 2021, which is based upon and claims priority to Chinese Patent Application No. 202110435173.6, filed on Apr. 22, 2021, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBKY077_Sequence Listing.txt, created on 05/02/2022 and is 5,542 bytes in size.

TECHNICAL FIELD

The present invention belongs to the field of microbiology, and in particular, relates to use of citronellol in preparing a preparation for promoting an expression of a virulence gene toxA of *Pseudomonas aeruginosa*.

BACKGROUND

*Pseudomonas aeruginosa* often induces cystic fibrosis (CF), meningitis, abscesses, soft tissue infections, urinary tract infections, corneal infections, ventilator-associated pneumonia, and catheter-related infections. Infections induced thereby are highly likely to occur in convalescent patients with low immunity, leading to postoperative wound infections. Acute infections with *Pseudomonas aeruginosa* can be treated with antibiotics, but when *Pseudomonas aeruginosa* successfully colonizes in a host, the acute infections would easily turn into chronic infections, showing a permanent biofilm form to result in worsening of organ infections in the host. It is difficult to eradicate *Pseudomonas aeruginosa* completely with a traditional antibacterial therapy.

The pathogenicity of *Pseudomonas aeruginosa* depends on the degree of damage to the host by its virulence factor. An exotoxin A of *Pseudomonas aeruginosa* has a protein structure mainly including three regions, which show different functions in inhibition of protein synthesis after a toxin enters a cell. After the structure and function of the exotoxin A of *Pseudomonas aeruginosa* have been clearly understood, some scientists have begun to modify and utilize the exotoxin A by genetic engineering, making it medically useful and applicable to clinical medicine.

At present, the exotoxin A of *Pseudomonas aeruginosa* has been medically used as follows: an antibody is bonded to the exotoxin A to create an immunotoxin, which, with the antibody as a mediator, enters certain specific cells to inhibit protein synthesis in these cells, thereby achieving the purpose of destroying the growth of these specific cells, in particular in the research of anti-cancer drugs; the exotoxin A is used to develop a *Pseudomonas aeruginosa* vaccine, which is a good vaccine protein that can be applied to vaccine research and development regardless of being prepared into a non-toxic exotoxin-A fragment or fused with other antigens; and in respect of the treatment of liver cancer cells, the exotoxin A has a special function of carrying proteins or DNAs into cells, whereby excellent gene therapy tools or protein therapy drugs can be developed.

Citronellol is a monoterpene with the molecular formula $C_{10}H_{20}O$. It appears as a colorless liquid with a sweet rose fragrance. Dextro- or laevo-citronellol and racemates thereof can be found in natural plant essential oils. Dextro-citronellol is mainly found in rue oil, citronella oil, and lemon *eucalyptus* oil; and laevo-citronellol is mainly found in rose oil and essential oils of *Pelargonium* plants.

SUMMARY

An object of the present invention is to provide use of citronellol in preparing a preparation for promoting an expression of a virulence gene toxA of *Pseudomonas aeruginosa.*

Based on experiments, the present invention demonstrates that citronellol slightly inhibits the growth of *Pseudomonas aeruginosa* PAO1 strains, and can promote the transcription of *Pseudomonas aeruginosa* toxA, which can increase the yield of an exotoxin A, namely, an encoded product of toxA.

Therefore, the object of the present invention is to provide the use of the citronellol in preparing the preparation for promoting the expression of the virulence gene toxA of *Pseudomonas aeruginosa.*

The *Pseudomonas aeruginosa* is preferably *Pseudomonas aeruginosa* PAO1.

Preferably, the use of the citronellol in preparing a preparation for promoting the production of an exotoxin A in *Pseudomonas aeruginosa* is provided.

Preferably, the citronellol is β-citronellol.

Preferably, a concentration of the citronellol in a *Pseudomonas aeruginosa* culture solution is 0.313-2.5 μL/mL, and further preferably 1.25 μL/mL.

It is found in the present invention that the citronellol at the concentration of 0.313-2.5 μL/mL slightly inhibits the growth of *Pseudomonas aeruginosa* PAO1 strains, and can promote the transcription of *Pseudomonas aeruginosa* toxA, which can increase the yield of an exotoxin A, namely an encoded product of toxA. Therefore, the citronellol is applicable to the promotion of the transcription of the *Pseudomonas aeruginosa* toxA, so as to improve the yield of the exotoxin A.

BRIEF DESCRIPTION OF THE DRAWINGS

FIG. 1 shows growth curves of *Pseudomonas aeruginosa* PAO1 under the action of citronellol; and FIG. 2 shows effects of citronellol on the expressions of key genes of a quorum-sensing system of *Pseudomonas aeruginosa* and virulence genes regulated thereby.

DETAILED DESCRIPTION OF THE EMBODIMENTS

The embodiments below are intended to further explain the present invention, instead of limiting the present invention.

Embodiment 1

Preparation of PAO1[(*Pseudomonas aeruginosa*) PAO1] bacterial suspension: a culture solution of *Pseudomonas aeruginosa* PAO1 in an exponential growth phase was sampled, centrifuged, washed once with a PBS buffer, resuspended in PBS, and diluted to $10^8$ CFU/mL to obtain the PAO1 bacterial suspension.

1. Experiment on effects of citronellol on the growth of *Pseudomonas aeruginosa* PAO1

An LB culture medium and citronellol (0-citronellol) were added to test tubes respectively, and the PAO1 bacterial suspension in the exponential growth phase was inoculated to reach a total volume of 10 mL respectively. The bacterial concentration of PAO1 was each $10^{6+}$ CFU/mL, and the concentration of citronellol was 0 (control), 0.313 μL/mL, 0.625 μL/mL, 1.25 μL/mL, and 2.5 μL/mL, respectively. Samples from several test groups were added to a honeycomb culture plate dedicated to an automatic growth curve analyzer (Bioscreen C), and 350 μL of culture solution was added to each well, with three parallel for each test group. The honeycomb culture plate was placed in the automatic growth curve analyzer, and cultured over shaking at 37° C. for 3 days, and $OD_{600}$ was measured every hour. Taking $OD_{600}$ as the ordinate and a culture time as the abscissa, the growth curve of PAO1 under the action of citronellol was drawn to study the effect of the citronellol on the growth of PAO1. The results were shown as in FIG. 1.

2. Experiment on effects of citronellol on the expression of key genes in a quorum-sensing system of *Pseudomonas aeruginosa* and virulence genes regulated thereby The PAO1 bacterial suspension in a logarithmic growth phase was added to 50 mL of sterile LB liquid culture medium to reach a final concentration of $10^6$ CFU/mL for the bacterial solution. Citronellol (β-citronellol) was added to reach the final concentrations of 0 (three biological replicates in the control group were named A1, A2, and A3, respectively) and 1.25 μL/mL (three biological replicates in the test groups were named B1, B2, B3). Each group was cultured at 37° C. and 180 rpm for 5 h, and centrifuged to collect bacteria, which were then quick-frozen at −80° C. for later use.

Total RNAs were extracted from the bacteria by a Trizol (Thermo Fisher Scientific) kit.

After extraction, the purity of the RNAs were detected with an ultra-micro spectrophotometer (Implen, Munich, Germany). An A260/A280 value of each RNA sample should be between 1.8 and 2.0. Reverse transcription and real-time fluorescent quantitative PCR amplification were carried out by using a PrimeScript RT Master Mix kit (Takara, Dalian, China) and an ETC 811 PCR instrument (Eastwin Life Sciences, Inc.). A q-PCR reaction system included Takara SYBR Premix Ex TaqII (Tli RNaseH Plus) (Code No. RR820A), and PCR procedures included: pre-denaturation at 95° C. for 30 s; and denaturation at 95° C. for 5 s and annealing at 60° C. for 34 s, 40 cycles. Based on 10 gene sequences published on the website of GenBank, primers for q-PCR were designed by using software Primer Premier 5.0, and at the same time, a 16S rRNA gene was used as an internal reference gene. The primer sequence parameters are shown in Table 1.

TABLE 1

Genes and printer sequences thereof used in real-time fluorescent quantitative PCR

| Gene name | Locus | Gene description | Primer sequences (5'→3') | SEQ ID NO: |
|---|---|---|---|---|
| 16S rRNA | PA5369.5 | 16S ribosomal RNA | GCGCAACCCTTGTCCTTAGTT (F) | 1 |
|  |  |  | TGTCACCGGCAGTCTCCTTAG (R) | 2 |
| lasI | PA1432 | Acyl-homoserine-lactone synthase | TGCGTGCTCAAGTGTTCAAGG (F) | 3 |
|  |  |  | CGGCTGAGTTCCCAGATGTGC (R) | 4 |
| lasR | PA1430 | Transcriptional regulator LasR | GACCAGTTGGGAGATATCGGTTA (F) | 5 |
|  |  |  | TCCGCCGAATATTTCCCATA (R) | 6 |
| rhlI | PA3476 | Acyl-homoserine-lactone synthase | AAACCCGCTACATCGTCGC (F) | 7 |
|  |  |  | TCTCGCCCTTGACCTTCTGC (R) | 8 |
| rhlR | PA3477 | Transcriptional regulator RhlR | ATCGCCATCATCCTGAGCATT (F) | 9 |
|  |  |  | TCGGAGGACATACCAGCACAC (R) | 10 |
| pqsA | PA0996 | Anthranilate-CoA ligase | GCAATACACCTCGGGTTCCA (F) | 11 |
|  |  |  | TCCGCTGAACCAGGGAAAGA (R) | 12 |
| pqsR | PA1003 | Transcriptional regulator | TCGTTCTGCGATACGGTGAG (F) | 13 |
|  |  |  | GCACTGGTTGAAGCGGGAG (R) | 14 |
| lasA | PA1871 | Protease LasA | GCCGCTGAATGACGACCTGT (F) | 15 |
|  |  |  | TCAGGGTCAGCAACACTT (R) | 16 |
| lasB | PA3724 | Elastase LasB | AAGGCCTTGCGGGTATCC (F) | 17 |
|  |  |  | CGTGTACAACCGTGCGTTCT (R) | 18 |
| phzM | PA4209 | Phenazine-specific methyltransferase | GAATGGAAGTCCCGTTGC (F) | 19 |
|  |  |  | GCCCTCGACATCCCTCA (R) | 20 |
| chiC | PA2300 | Chitinase | CTGGGAGTTCCGCAAGCGTTAC (F) | 21 |
|  |  |  | ATCGGTGGCGGTGACGAAATAG (R) | 22 |
| toxA | PA1148 | Exotoxin A | CCCGGCGAAGCATGAC (R) | 23 |
|  |  |  | GGGAAATGCAGGCGATGA (R) | 24 |
| pslB | PA2232 | Biofilm formation protein PslB | CAACGAATCCACCTTCATCC (F) | 25 |
|  |  |  | ACTCGCCGCTCTGTACCTC (R) | 26 |

Experimental Results:

The results on the growth curves of *Pseudomonas aeruginosa* PAO1 under the action of citronellol at different concentrations are shown in FIG. 1. The experimental results show that the growth of strains is slightly inhibited after PAO1 cells are treated with the citronellol. The citronellol treatment groups at different concentrations exhibit no significant difference in a lag phase and a logarithmic growth phase on the PAO1 growth curves, but have a certain effect on a stable phase and a decay phase. It can be seen from the graph that the time points when the absorbance values of the culture solutions in the treatment groups at different concentrations differ greatly: 26 h for the treatment group at 0.313 μL/mL, 37 h for the treatment group at 0.625 μL/mL, 39 h for the treatment group at 1.25 μL/mL, and 48 h for the treatment group at 2.5 μL/mL. The higher the concentration of the citronellol, the longer the time for the absorbance value of the culture solution to reach the maximum value, and the longer the stable phase. The citronellol at 0.313, 0.625, 1.25 and 2.5 μL/mL shows a certain yet weak inhibitory effect on the growth of PAO1. Therefore, citronellol slightly inhibits the growth of PAO1.

Figure 2:
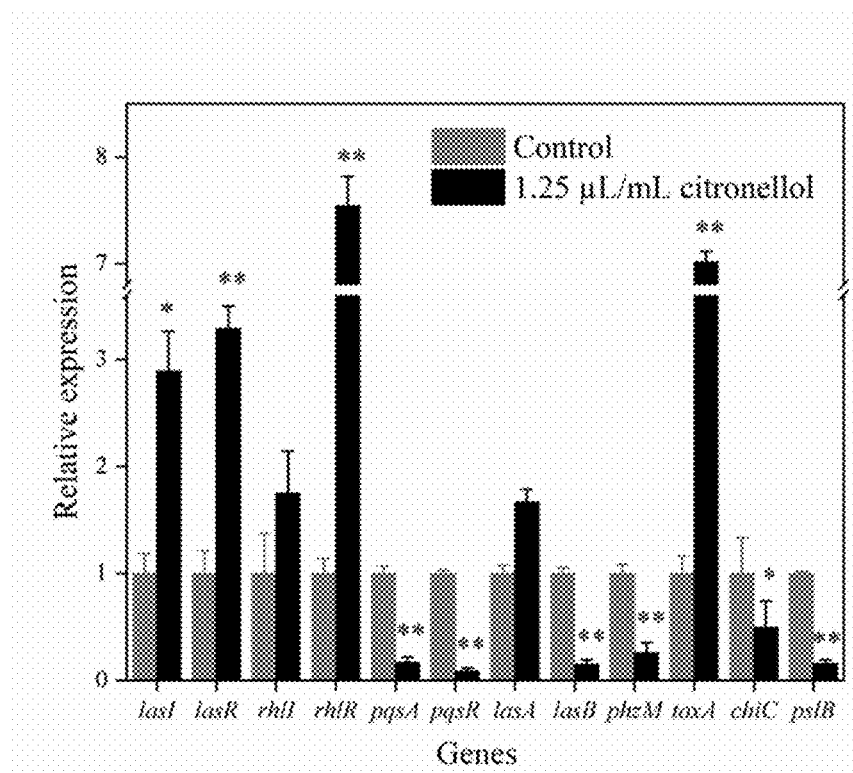

FIG. 2 shows changes in the expression levels of key genes in the quorum-sensing system of PAO1 cells and virulence genes associated therewith after these cells are treated with 1.25 μL/mL citronellol for 5 h. The expressions of a signaling molecule synthase gene lasI and a signaling molecule receptor protein gene lasR of a las system are significantly up-regulated. The transcription levels of a signaling molecule receptor protein gene rhIR in a rhI system is also significantly up-regulated, but the transcription level of a signaling molecule synthase gene rhII changes a little. The expressions of a signaling molecule synthase gene pgsA and a signaling molecule receptor protein gene pqsR of a pqs system are both significantly down-regulated. The transcriptions of virulence genes lasB, phzM, chiC and psIB are all inhibited by the citronellol; the transcription level of toxA was significantly up-regulated; and the transcription level of lasA is also up-regulated, but with a less significant change. Therefore, the citronellol promotes the transcription of *Pseudomonas aeruginosa* toxA.

In summary, the experimental results demonstrate that the citronellol slightly inhibits the growth of *Pseudomonas aeruginosa* PAO1 strains (FIG. 1), and can promote the transcription of *Pseudomonas aeruginosa* toxA (FIG. 2), which improves the yield of the exotoxin A, namely, the encoded product of toxA.

What is claimed is:

1. A method of using citronellol to promote expression of a virulence gene toxA in *Pseudomonas aeruginosa*, comprising:
   preparing a liquid LB culture medium with citronellol, wherein the concentration of the citronellol in the culture medium is 1.25 μL/mL;
   inoculating the medium with a bacterial suspension of *Pseudomonas aeruginosa* in the exponential growth phase, wherein the expression of the virulence gene toxA results in production of an exotoxin A in the *Pseudomonas aeruginosa*;
   up-regulating expression of a signaling molecule synthase gene lasI and a signaling molecule receptor protein gene lasR of a las system;
   up-regulating expression of a signaling molecule receptor protein gene rhIR in a rhI system;
   inhibiting expression of a signaling molecule synthase gene pqsA and a signaling molecule receptor protein gene pqsR of a pqs system; and
   inhibiting expression of virulence genes lasB, phzM, chiC and psIB.

2. The method of using citronellol to promote expression of a virulence gene toxA in *Pseudomonas aeruginosa* according to claim 1, wherein the *Pseudomonas aeruginosa* is the strain *Pseudomonas aeruginosa* PAO1.

3. The method of using citronellol to promote expression of a virulence gene toxA in *Pseudomonas aeruginosa* according to claim 1, wherein the citronellol is p-citronellol.

4. The method according to claim 2, wherein the citronellol is β-citronellol.

5. The method of using citronellol to promote expression of a virulence gene toxA in *Pseudomonas aeruginosa* according to claim 1, further comprising:
   incubating the bacterial suspension together with the citronellol; and
   collecting the expressed exotoxin A from the culture medium.

* * * * *

SEQUENCE LISTING

```
<160> NUMBER OF SEQ ID NOS: 26

<210> SEQ ID NO 1
<211> LENGTH: 21
<212> TYPE: DNA
<213> ORGANISM: Artificial Sequence
<220> FEATURE:
<223> OTHER INFORMATION: Sequence is synthesized

<400> SEQUENCE: 1
gcgcaaccct tgtccttagt t                                               21

<210> SEQ ID NO 2
<211> LENGTH: 21
<212> TYPE: DNA
<213> ORGANISM: Artificial Sequence
<220> FEATURE:
<223> OTHER INFORMATION: Sequence is synthesized

<400> SEQUENCE: 2
tgtcaccggc agtctcctta g                                               21

<210> SEQ ID NO 3
<211> LENGTH: 21
<212> TYPE: DNA
<213> ORGANISM: Artificial Sequence
<220> FEATURE:
<223> OTHER INFORMATION: Sequence is synthesized

<400> SEQUENCE: 3
tgcgtgctca agtgttcaag g                                               21

<210> SEQ ID NO 4
<211> LENGTH: 21
<212> TYPE: DNA
<213> ORGANISM: Artificial Sequence
<220> FEATURE:
<223> OTHER INFORMATION: Sequence is synthesized

<400> SEQUENCE: 4
```
cggctgagtt cccagatgtg c                                              21

<210> SEQ ID NO 5
<211> LENGTH: 23
<212> TYPE: DNA
<213> ORGANISM: Artificial Sequence
<220> FEATURE:
<223> OTHER INFORMATION: Sequence is synthesized

<400> SEQUENCE: 5
gaccagttgg gagatatcgg tta                                            23

<210> SEQ ID NO 6
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 6
tccgccgaat atttcccata                                                20

<210> SEQ ID NO 7
<211> LENGTH: 19
<212> TYPE: DNA
<213> ORGANISM: Artificial Sequence
<220> FEATURE:
<223> OTHER INFORMATION: Sequence is synthesized

<400> SEQUENCE: 7
aaacccgcta catcgtcgc                                                 19

<210> SEQ ID NO 8
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 8
tctcgccctt gaccttctgc                                                20

<210> SEQ ID NO 9
<211> LENGTH: 21
<212> TYPE: DNA
<213> ORGANISM: Artificial Sequence
<220> FEATURE:
<223> OTHER INFORMATION: Sequence is synthesized

<400> SEQUENCE: 9
atcgccatca tcctgagcat t                                              21

<210> SEQ ID NO 10
<211> LENGTH: 21
<212> TYPE: DNA
<213> ORGANISM: Artificial Sequence
<220> FEATURE:
<223> OTHER INFORMATION: Sequence is synthesized

<400> SEQUENCE: 10
tcggaggaca taccagcaca c                                              21

<210> SEQ ID NO 11
<211> LENGTH: 20
<212> TYPE: DNA
<213> ORGANISM: Artificial Sequence

```
<220> FEATURE:
<223> OTHER INFORMATION: Sequence is synthesized

<400> SEQUENCE: 11
gcaatacacc tcgggttcca                                               20

<210> SEQ ID NO 12
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 12
tccgctgaac cagggaaaga                                               20

<210> SEQ ID NO 13
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 13
tcgttctgcg atacggtgag                                               20

<210> SEQ ID NO 14
<211> LENGTH: 19
<212> TYPE: DNA
<213> ORGANISM: Artificial Sequence
<220> FEATURE:
<223> OTHER INFORMATION: Sequence is synthesized

<400> SEQUENCE: 14
gcactggttg aagcgggag                                                19

<210> SEQ ID NO 15
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 15
gccgctgaat gacgacctgt                                               20

<210> SEQ ID NO 16
<211> LENGTH: 18
<212> TYPE: DNA
<213> ORGANISM: Artificial Sequence
<220> FEATURE:
<223> OTHER INFORMATION: Sequence is synthesized

<400> SEQUENCE: 16
tcagggtcag caacactt                                                 18

<210> SEQ ID NO 17
<211> LENGTH: 18
<212> TYPE: DNA
<213> ORGANISM: Artificial Sequence
<220> FEATURE:
<223> OTHER INFORMATION: Sequence is synthesized

<400> SEQUENCE: 17
aaggccttgc gggtatcc                                                 18
```

```
<210> SEQ ID NO 18
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 18
cgtgtacaac cgtgcgttct                                             20

<210> SEQ ID NO 19
<211> LENGTH: 18
<212> TYPE: DNA
<213> ORGANISM: Artificial Sequence
<220> FEATURE:
<223> OTHER INFORMATION: Sequence is synthesized

<400> SEQUENCE: 19
gaatggaagt cccgttgc                                               18

<210> SEQ ID NO 20
<211> LENGTH: 17
<212> TYPE: DNA
<213> ORGANISM: Artificial Sequence
<220> FEATURE:
<223> OTHER INFORMATION: Sequence is synthesized

<400> SEQUENCE: 20
gccctcgaca tccctca                                                17

<210> SEQ ID NO 21
<211> LENGTH: 22
<212> TYPE: DNA
<213> ORGANISM: Artificial Sequence
<220> FEATURE:
<223> OTHER INFORMATION: Sequence is synthesized

<400> SEQUENCE: 21
ctgggagttc cgcaagcgtt ac                                          22

<210> SEQ ID NO 22
<211> LENGTH: 22
<212> TYPE: DNA
<213> ORGANISM: Artificial Sequence
<220> FEATURE:
<223> OTHER INFORMATION: Sequence is synthesized

<400> SEQUENCE: 22
atcggtggcg gtgacgaaat ag                                          22

<210> SEQ ID NO 23
<211> LENGTH: 16
<212> TYPE: DNA
<213> ORGANISM: Artificial Sequence
<220> FEATURE:
<223> OTHER INFORMATION: Sequence is synthesized

<400> SEQUENCE: 23
cccggcgaag catgac                                                 16

<210> SEQ ID NO 24
<211> LENGTH: 18
<212> TYPE: DNA
<213> ORGANISM: Artificial Sequence
<220> FEATURE:
<223> OTHER INFORMATION: Sequence is synthesized
```

```
<400> SEQUENCE: 24
gggaaatgca ggcgatga                                                    18

<210> SEQ ID NO 25
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 25
caacgaatcc accttcatcc                                                  20

<210> SEQ ID NO 26
<211> LENGTH: 19
<212> TYPE: DNA
<213> ORGANISM: Artificial Sequence
<220> FEATURE:
<223> OTHER INFORMATION: Sequence is synthesized

<400> SEQUENCE: 26
actcgccgct ctgtacctc                                                   19
```